(12) United States Patent
Balmelli et al.

(10) Patent No.: US 8,518,380 B2
(45) Date of Patent: Aug. 27, 2013

(54) PROPHYLACTIC CLEANING PRODUCT AND METHOD OF PACKAGING

(75) Inventors: Patrizia Balmelli, Gentilino (CH); Beat Kilcher, Bosco Luganese (CH)

(73) Assignee: KerrHawe SA, Bioggio (CH)

( * ) Notice: Subject to any disclaimer, the term of this patent is extended or adjusted under 35 U.S.C. 154(b) by 960 days.

(21) Appl. No.: 11/950,528

(22) Filed: Dec. 5, 2007

(65) Prior Publication Data
US 2008/0160055 A1 Jul. 3, 2008

Related U.S. Application Data

(60) Provisional application No. 60/882,723, filed on Dec. 29, 2006.

(51) Int. Cl.
| | |
|---|---|
| *A61Q 11/00* | (2006.01) |
| *A61K 8/02* | (2006.01) |
| *A61K 8/21* | (2006.01) |
| *B65B 1/04* | (2006.01) |

(52) U.S. Cl.
USPC .................. 424/49; 424/401; 424/52; 53/469

(58) Field of Classification Search
USPC ................................ 424/401, 49, 52; 53/469
See application file for complete search history.

(56) References Cited

U.S. PATENT DOCUMENTS

| | | | |
|---|---|---|---|
| 3,641,238 A * | 2/1972 | Januszewski | 424/49 |
| 5,266,304 A * | 11/1993 | Baffelli et al. | 424/49 |
| 5,597,553 A * | 1/1997 | Baffelli et al. | 424/49 |
| 6,379,654 B1 * | 4/2002 | Gebreselassie et al. | 424/50 |
| 6,576,225 B1 | 6/2003 | Kilcher et al. | |
| 6,712,898 B2 | 3/2004 | Palm et al. | |
| 7,125,432 B2 * | 10/2006 | Huang | 51/308 |

FOREIGN PATENT DOCUMENTS

| | | |
|---|---|---|
| EP | 1050293 A1 | 11/2000 |
| WO | 2004064795 A1 | 8/2004 |

OTHER PUBLICATIONS

Wülknitz, P., Cleaning Power and Abrasivity of European Toothpastes, Adv. Dent. Res. 11(4):576-579, Nov. 1997.
European Patent Office, European Search Report of corresponding EP Application No. 07254984.3 dated Apr. 17, 2008, 4 pp.

* cited by examiner

*Primary Examiner* — Rachael E Bredefeld
(74) *Attorney, Agent, or Firm* — Wood, Herron & Evans, LLP

(57) ABSTRACT

A prophylactic (prophy) paste composition comprising about 40 percent by weight to about 55 percent by weight expanded perlite comprising perlite granules in the range of about 20 μm to about 70 μm and floaters. The prophy paste composition further comprises no more than 5 percent by weight of a surfactant, and greater than about 10 percent by weight water. In some embodiments, the inventive paste also contains a humectant and optionally, may contain coloring agents, preservative agents, alcohol, flavoring agents, viscosity increasing agents, and sodium fluoride. The present invention also provides methods for controlling the floater content of the expanded perlite used in the inventive paste and methods of packaging the expanded perlite paste composition in a tube. The present invention also provides a prophy paste product comprising the inventive prophy paste contained within a squeezable tube.

18 Claims, 1 Drawing Sheet

PROPHYLACTIC CLEANING PRODUCT AND METHOD OF PACKAGING

CROSS REFERENCE TO RELATED APPLICATIONS

This application claims the benefit of the filing of U.S. Provisional Patent Application Ser. No. 60/882,723, filed Dec. 29, 2006, entitled CLEANIC IN TUBE, which is fully incorporated by reference herein.

FIELD OF THE INVENTION

The present invention relates to a cleaning and polishing paste for the enamel and dentine surfaces of teeth and, more particularly, to a dental cleaning and polishing paste containing expanded perlite that can be dispensed from a tube.

BACKGROUND

Abrasive substances have been included in conventional dentifrice compositions in order to remove various deposits, including pellicle film, from the surfaces of teeth. Pellicle film is tightly adherent and often contains brown or yellow pigments that impart an unsightly appearance to the teeth. While cleaning is important, the abrasive should not be so aggressive so as to damage the teeth. Ideally, an effective dentifrice abrasive material maximizes pellicle film removal while causing minimal abrasion and damage to the hard tooth tissues.

In the past, the polishing paste used by a dentist or hygienist was packaged in a jar and the prophy cup attached to a dental hand piece was dipped into the jar and then the prophy cup was applied to the teeth. With the advent of potentially fatal diseases that may be present in an oral cavity, the use of a common jar as a source of polishing material for multiple patients was no longer medically acceptable. To avoid this potential medical problem, the polishing compound was packaged in small sealed containers with enough polishing compound to polish the teeth of a single patient. After a one-time use, such a container was disposed of as waste to prevent the spread of disease to other patients. However, such waste is not ideal.

Paste formulations that are stable could potentially meet a number of requirements, including the ability to be transferred out of a container (such as a tube) via pressure (i.e., squeezing of the tube) as a dimensionally stable paste and to return to its previous state upon removal of such pressure, the ability to be transferred in such a manner to an applicator easily and without flow out of the tube during and after such transference, the propensity to remain dimensionally stable on the applicator prior to use, a reduction of spattering, and the proper feel of the paste in the mouth, at least, for the benefit of the user.

A number of water-insoluble, abrasive polishing agents have been used or described for dentifrice compositions. These abrasive polishing agents include natural and synthetic abrasive particulate materials. The generally known synthetic abrasive polishing agents include amorphous precipitated silicas and silica gels and precipitated calcium carbonate (PCC). Other abrasive polishing agents for dentifrices have included chalk, magnesium carbonate, dicalcium phosphate and its dihydrate forms, calcium pyrophosphate, zirconium silicate, potassium metaphosphate, magnesium orthophosphate, tricalcium phosphate, perlite, and the like.

Conventional processing of perlite consists of comminution of the ore (crushing and grinding), screening, thermal expansion, milling, and air size separation of the expanded material to meet the specification of the finished product. For example, perlite ore is crushed, ground, and separated to a predetermined particle size range (e.g., passing 30 mesh), then the separated material is heated in air at a temperature of 870°-1100° C. in an expansion furnace, where the simultaneous softening of the glass and vaporization of contained water leads to rapid expansion of glass particles to form a frothy glass material with a bulk volume up to 20 times that of the unexpanded ore. The expanded perlite is then air separated to meet the size specification of the final product. The expanded perlite product may further be milled and separated for use as filter aid or filler material.

Perlite-containing pastes have not been capable of being packaged in tubes because the paste is too viscous and dry and thus, cannot be dosed from the tube with a reasonable applied pressure. Therefore, a perlite-containing paste composition that is capable of being dosed from a tube is needed.

SUMMARY OF THE INVENTION

The present invention provides a prophylactic (prophy) paste composition comprising about 40 percent by weight to about 55 percent by weight expanded perlite that comprises perlite granules having a mean grain size of about 20-70 μm, and floaters. The prophy paste composition further comprises no more than about 5 percent by weight of a surfactant, and greater than about 10 percent by weight water. In some embodiments, the inventive paste also contains a humectant and optionally, may contain coloring agents, preservative agents, alcohol, flavoring agents, viscosity increasing agents, and sodium fluoride.

The present invention also provides methods for controlling the floater content of the expanded perlite used in the inventive paste and methods of packaging the expanded perlite paste composition in a squeezable tube. The present invention also provides a prophy paste product comprising the inventive prophy paste contained within a squeezable tube.

DETAILED DESCRIPTION

Figure 1:
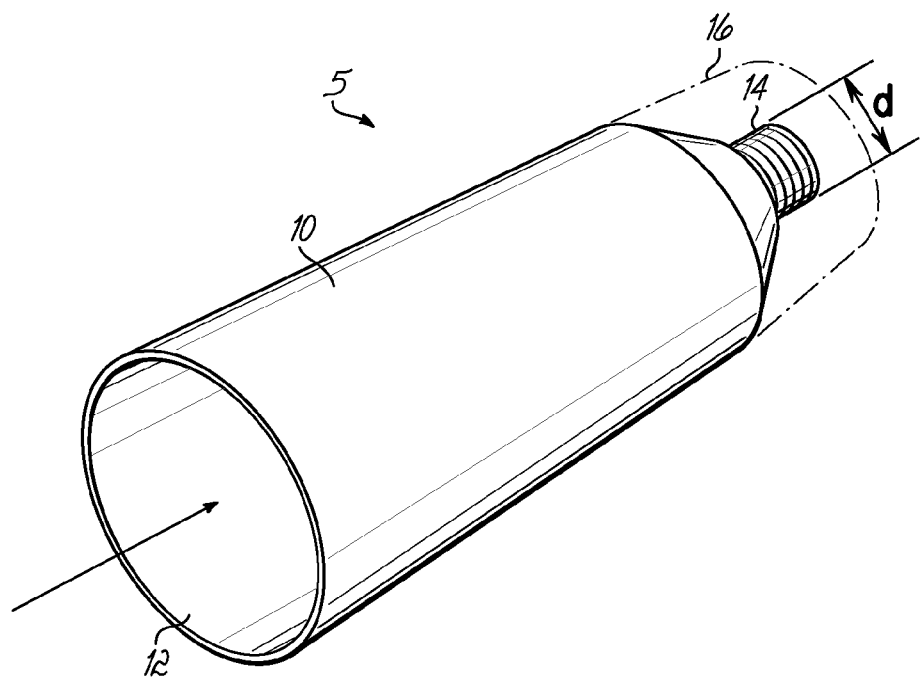
FIG. 1 shows in perspective, schematic view a squeezable tube in one configuration for receiving a prophylactic paste of the invention.

During a prophylaxis treatment by a dentist or a hygienist, the final step is usually a cleaning and polishing procedure using a prophylactic (prophy) paste in conjunction with a rotatable prophy cup attached to a conventional dental hand piece.

The present invention provides for a prophy paste composition comprising expanded perlite, and a method of formation of the inventive paste.

In one embodiment, a prophylactic paste for cleaning and polishing is provided and comprises, as the sole cleaning and polishing body, expanded perlite in the range of about 40 percent by weight to about 55 percent by weight, wherein the expanded perlite is comprised of perlite powder and floaters. The perlite powder has a mean grain size of at least about 20 μm, for example at least about 30 μm. Further, the perlite powder has a mean grain size of about 70 μm or less, for example about 60 μm or less. The paste further comprises about 5 percent by weight or less of a surfactant and greater than about 10 percent by weight water. Also, the present inventive composition provides a prophy paste that can be packaged in a tube, due to the relatively low viscosity of the composition.

Perlite is a generic term for naturally occurring siliceous rock. The distinguishing feature that sets perlite apart from other volcanic glasses is that when heated to a suitable point in its softening range, it expands from four to twenty times its original volume. This expansion is due to the presence of about two to about six percent water in the crude perlite rock. When quickly heated to above about 1600° F. (871° C.), the crude rock pops in a manner similar to popcorn as the water vaporizes and creates countless tiny bubbles, which account for the physical properties of expanded perlite.

Since perlite is a natural material, the compositions of batches taken from different ore bodies or even different parts of the same ore body will normally vary, sometimes widely, but normally within fairly well defined limits. Typically, perlite contains 71% to 75% $SiO_2$, 12% to 18% $Al_2O_3$, 7% to 9% $K_2O$ and $Na_2O$ with the remainder being a wide variety of other oxides and elements including materials such as calcium, iron, magnesium and titanium oxides.

The expanded perlite normally contains a significant amount of material called floaters, which are expanded perlite particles that often contain entrapped air. As the name suggests, floaters quickly float to the surface of liquid rather than remain buoyantly suspended in it. The quantity of floaters in a perlite batch has been expressed in Darcy value. The Darcy value describes the permeability of filter aids and is represented by the Darcy equation:

$$V = K\frac{\Delta \rho A}{h\eta}$$

where V is flow rate (m$^3$/s), $\Delta\rho$ is pressure drop (Pa), A is filter area (m$^2$), h is height of the fixed bed (m), $\eta$ is viscosity (Pa s), and K is a constant for permeability characterization (m$^2$). The constant K is 1 Darcy if a sample of 1 cm thickness and 1 cm$^2$ filter area shows, for a liquid with a viscosity of 1 mPas at a flow rate of 1 cm$^3$/s, a pressure drop of 1 bar.

The floater content has a negative effect on some perlite applications, such as filter aids, and therefore, has been minimized during the processing of perlite for many applications.

However, in the present invention, it was determined that the amount of floaters in the prophy paste had a significant impact on the manufacturing process as well as the sandiness as perceived by the patient. For instance, with increased floater amounts, the viscosity of the paste decreased and the sandiness increased. As discussed above, prior prophy paste could not be packaged in tubes because the paste was too viscous and dry. However, by optimizing the amount of floaters in the paste, viscosity can be decreased to allow packaging in tubes and the ability to dispense from a tube with acceptable pressure. The optimization of the floater content also provides for acceptable sandiness. In one embodiment, the amount of floaters, as expressed in Darcy value, in the inventive paste is less than about 3. In another embodiment, the amount of floaters, as expressed in Darcy value, in the inventive paste is less than about 2. Expressed differently, a Darcy value of less than 2 equates to less than about 5% by weight floaters in the perlite. In another embodiment, the amount of floaters, as expressed in Darcy value, in the inventive paste is in the range of about 0.1 to about 3.

As described above, the expanded perlite is composed of two physical forms, granules and floaters. In one embodiment, the size of perlite granules in the inventive paste is in the range of about 20 μm to about 70 μm. In another embodiment, the size of the perlite granules is in the range of about 30 μm to about 60 μm. In another embodiment, the size of the perlite granules is in the range of about 50 μm to about 60 μm. In one embodiment, the size of the floaters ranges from about 50 μm to about 2000 μm.

The inventive paste also contains at least one surfactant. An example of a suitable surfactant is PEG 40 castor oil, e.g. Eumulgin® RO 40 (Cognis Deutschland GmbH & Co., Germany). In one embodiment, the surfactant comprises about 5 percent by weight or less of the inventive paste. In another embodiment, the surfactant component of the inventive paste is in the range of about 1 percent by weight to about 5 percent by weight of the paste.

The inventive paste also contains water. In one embodiment, the paste contains greater than about 10 percent by weight of water, for example, about 11 percent by weight or more. In another embodiment, the inventive paste contains less than about 35 percent by weight water. In another embodiment, the inventive paste contains less than about 25 percent by weight water. In another embodiment, the paste contains water in the range of about 11 percent by weight to about 25 percent by weight of the paste.

According to one embodiment, the prophy paste of the present invention also contains at least one humectant. In one embodiment, the humectant is glycerin 1.26 EP (Georges Walter). In one embodiment, the humectant is in the range of about 26.5 percent by weight to about 36.5 percent by weight in the paste. The combination of water and humectant in some embodiments provides an ability to control the viscosity of the paste and a shortened production time.

In certain embodiments, the prophy paste of the invention may also include additional components such as a coloring agent, a preservative agent, an alcohol, a flavoring agent, a viscosity-increasing agent, and sodium fluoride. Examples of coloring agents are known to one skilled in the art. In embodiments where a coloring agent is present in the paste, the coloring agent is no greater than about 3 percent by weight of the paste. Examples of preservative agents are known to one skilled in the art. In embodiments where a preservative agent is present in the paste, the preservative agent is no greater than about 2 percent by weight of the paste. An example of an alcohol that may be used in the present invention is ethyl alcohol. In embodiments where an alcohol is present in the paste, the alcohol is no greater than about 2 percent by weight of the paste. Examples of flavoring agents are known to one skilled in the art. In embodiments where a flavoring agent is present in the paste, the flavoring agent is no greater than about 3 percent by weight of the paste. Examples of viscosity increasing agents include cellulose gum, e.g. Walocell® (Wolff Walsrode, Germany) and Cekol® (CPKelco, San Diego Calif.). In embodiments where a viscosity-increasing agent is present in the paste, the viscosity-increasing agent is no greater than about 1.5 percent by weight of the paste. In embodiments where sodium fluoride is present in the paste, the sodium fluoride is no greater than about 3 percent by weight of the paste.

The abrasive and/or cleaning attributes of the prophy paste can be expressed using the standard dentifrice measurements pellicle cleaning ratio (PCR), relative dentin abrasion (RDA), and relative enamel abrasion (REA). In one embodiment, the inventive paste has a PCR value of greater than about 85. In one embodiment, the inventive paste has a RDA of less than about 265. In one embodiment, the inventive paste has a REA of less than about 8.

In one embodiment, the prophy paste of the present invention contains about 40 to about 55 percent by weight expanded perlite having a Darcy value in the range of about 0.1 to about 3, about 26.5 to about 36.5 percent by weight humectant, about 11 to about 35 percent by weight water, about 1 to about 5 percent by weight surfactant, up to about 3 percent by weight coloring agent, up to about 2 percent by weight preservative agent, up to about 2 percent by weight alcohol, up to about 3 percent by weight flavoring agent, up to about 1.5 percent by weight viscosity increasing agent, and up to about 3 percent by weight sodium fluoride.

The present invention also includes a method of forming the prophy paste by controlling the amount of floaters in the formulation. One method used to control floater content in the paste is the sorting and selection of perlite batches from the supplier with specific Darcy values. For instance, perlite batches that possess a Darcy value of less than 3 may be used, for example less than 2. In another method to control floater content in the paste, selective sieving of the perlite may be used. For instance, in one embodiment, a mesh size in the range from 20 to 50 may be used. In another embodiment, a mesh size in the range from 30 to 40 may be used. In another method to control floater content in the paste, the paste is subjected to calendaring to break down a portion of the floaters. For instance, the two roller wheels of the calendar may be separated in the range of about 0.05 mm to about 0.15 mm. In one embodiment, more than one of the above methods may be used to control the floater content in the paste.

The invention also provides for a prophylactic paste product and a method of packaging the prophylactic paste product in a squeezable tube. The prophylactic paste product comprises the prophylactic paste of the present invention contained within a squeezable tube. An example of a squeezable tube 5 and method of filling the same is depicted in perspective, schematic views in FIGS. 1 and 2, where one end of the tube body 10 includes a fill opening 12 and the other opposing end includes a dispense opening 14. The prophylactic paste of the invention is packaged into the squeezable tube 5 by filling through the fill opening 12, as indicated by the arrow in FIG. 1. After the tube body 10 is filled with the inventive prophylactic paste, the fill opening 12 is sealed by methods known in the art. The closed fill opening 18 is shown in FIG. 2.

Figure 2:
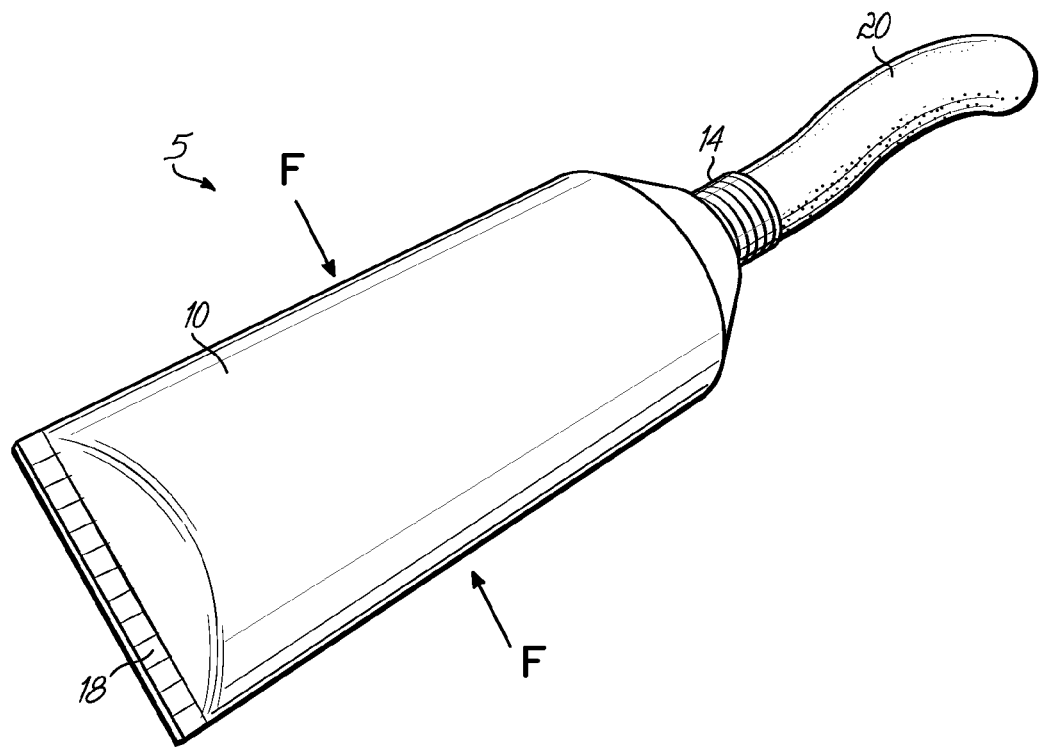
FIG. 2 shows in perspective, schematic view the squeezable tube in another configuration for dispensing the prophylactic paste of the invention.

The inventive prophylactic paste 20 is dispensed from the tube body 10 through the dispense opening 14 by applying a compressive force F to the sides of the tube body 10, as depicted in FIG. 2. In one embodiment, a compressive force F in the range of about 10 N to about 20 N is applied to dispense the paste. The dispense opening 14 has a diameter d that is consistent in size with known toothpaste tubes and the like, e.g., in the range of about 0.5 cm to about 2 cm. In another embodiment, the diameter d of the dispense opening 14 is in the range of about 0.7 cm to about 1.5 cm. Dispense opening 14 may include threading, if desired. As shown in FIG. 1, a cap 16 may optionally be attached to the dispense opening, for example, by screwing the cap 16 onto threading of the dispense opening 14, to seal the dispense opening until a practitioner is ready to dispense the paste. Other means of closing the dispense opening 14 are known to those skilled in the art, and are contemplated for use with this invention.

The prophy paste of the present invention provides numerous benefits including tube application of the paste, which makes dispensing of the paste into the prophy cup or ring easier, cleaner, and more convenient for the dentist or hygienist. The ability to dispense the paste from a tube also allows for increased hygiene compared to previous cartridge paste containers. In one embodiment, dispensing of the inventive paste from a tube may be achieved by applying a compressive force of about 10 N to about 20 N. This amount of squeezing is similar to that needed for dispensing toothpastes, namely 5 to 20 N of compressive force. As a comparison, common prophy pastes, when placed in a tube, cannot be extruded even with compressive forces of greater than 500 N. The present invention also provides benefits to the patient including less allergic potential compared to the cartridge paste dispensers, hygiene, less splattering, and better taste. From a production standpoint, the present invention decreases production costs due to decreased packaging time, increased stability resulting from a decreased danger of liquid separation on the surface or drying, and inclusion of water in the paste.

Example 1

Stained Pellicle Removal with Prophylaxis Pastes

Determination of the Cleaning Ability of Prophylaxis Pastes to Remove Stained Pellicle.

This laboratory test was developed in order to assess the ability of dentifrices to remove stained pellicle, i.e., to determine the cleaning ability of complete dentifrice formulations. Previous studies (J. Dent. Res., 61:1236, 1982) have indicated that the results of this test with dentifrice slurries compare favorably with those obtained in controlled clinical trials. Thus, the results of this test using dentifrice slurries may be considered to predict clinical findings with a reasonable degree of confidence. The use of prophylaxis systems in this model has not been given the same number of comparisons; however, it is reasonable to think the results would be similar.

Specimen Preparation

Bovine, permanent, central incisors were cut to obtain labial enamel specimens approximately 10×10 mm. The enamel specimens were then embedded in an autopolymerizing methacrylate resin so that only the enamel surfaces were exposed. The enamel surfaces were then smoothed and polished on a lapidary wheel and lightly etched to expedite stain accumulation and adherence. They were placed on a rotating rod (in 37° C. incubator) alternately exposing them to air and to a solution consisting of trypticase soy broth, tea, coffee, mucin, $FeCl_3$, and *Sarcina lutea*. The staining broth was changed and specimens rinsed twice daily for four days. After four days, a darkly stained pellicle film was apparent on the enamel surfaces. Specimens were then rinsed, allowed to air dry, and refrigerated until use. All products were tested using specimens prepared at the same time.

Scoring and Set-Up

The amount of in vitro stain was graded photometrically (Minolta CR 241, Chromameter) using only the L value of the L*a*b* scale. Specimens with scores between 23-42 (23 being more darkly stained) were used. On the basis of these scores, the specimens were divided into groups of 16 specimens each, with each group having the same average baseline score.

Test Procedure

The specimens were then individually mounted on a mechanical prophylaxis machine equipped with a Densco® Snap-on prophy cup, which rotated at 1500 rpm. Tension on the enamel surface was adjusted to 250 g. The prophy pastes were used as provided. The flour of pumice reference material was a slurry of 3 g abrasive and 2 ml of water. The prophy cup was filled with the appropriate paste and the specimens were prophied for 6 seconds. In this time, the cup covered the tooth surface twice. Following the prophy, the specimens were rinsed, blotted dry, and scored again for stain as previously described. The prophy cups were replaced after eight specimens resulting in the N of 16 per group.

Calculations

The difference between the individual specimen pre- and post-prophylaxis stain scores was determined and the mean and standard error calculated for the reference group in each study. The cleaning ratio for the reference material group was assigned a value of 100. The mean decrement for each reference group was divided into 100 to obtain a constant value to multiply times each individual test decrement within each study. The individual cleaning ratio of each specimen was then calculated (decrement×constant). The mean and SEM for each prophy paste group (N=16) was then calculated using the individual cleaning ratios. The larger the value of the cleaning ratio, the greater the amount of stained pellicle removed in this test.

Statistical Analysis

Statistical analyses were performed with a one-way analysis of variance model using Sigma Stat Software (3.0). Since significant differences were indicated, the individual means were analyzed by the Student Newman Keuls (SNK) Test.

The results are shown in Table 1 and Table 2 where the inventive paste is denoted as Sample S4, and various current commercial prophy paste formulations are denoted as Samples S1, S2, S3, and S5.

TABLE 1

| Dentrifice | N | Pellicle Cleaning Ratio |
| --- | --- | --- |
| Flour of Pumice | 15 | 100.00 ± 2.30* |
| Sample S4 | 16 | 89.49 ± 2.62** |
| Sample S2 | 16 | 89.46 ± 2.71** |
| Sample S3 | 16 | 88.74 ± 2.23** |
| Sample S5 | 16 | 87.29 ± 2.6** |
| Sample S1 | 16 | 84.97 ± 2.13** |

*Mean ± SEM
**No significant difference between groups (p > 0.05)

TABLE 2

(Sample S4)

| | L Value | | | |
| --- | --- | --- | --- | --- |
| Specimen | Pre | Post | Delta | Pellicle Cleaning Ratio |
| 68 | 30.3 | 67.2 | 36.9 | 104.6 |
| 95 | 30.5 | 68.6 | 38.1 | 108.1 |
| 20 | 31.7 | 63.4 | 31.7 | 89.9 |
| 42 | 31.9 | 68.2 | 36.3 | 103.0 |
| 24 | 32.8 | 60.5 | 27.8 | 78.8 |
| 92 | 33.1 | 65.7 | 32.6 | 92.5 |
| 21 | 34.2 | 67.3 | 33.0 | 93.7 |
| 90 | 34.5 | 61.0 | 26.5 | 75.2 |
| 40 | 34.8 | 65.8 | 31.0 | 88.0 |
| 35 | 35.1 | 68.6 | 33.5 | 95.1 |
| 73 | 36.9 | 65.9 | 29.1 | 82.5 |
| 59 | 37.1 | 66.3 | 29.2 | 82.7 |
| 9 | 37.7 | 63.2 | 25.6 | 72.6 |
| 17 | 37.9 | 67.4 | 29.5 | 83.8 |
| 25 | 39.1 | 68.6 | 29.5 | 83.6 |
| 62 | 39.6 | 74 | 34.5 | 97.8 |
| MEAN | 34.83 | 66.36 | 31.54 | 89.49 |
| STD. DEV. | 2.97 | 3.28 | 3.70 | 10.49 |
| STD. ERR. | 0.74 | 0.82 | 0.92 | 2.62 |

The results of Example 1 show that the sample S4 shows similar cleaning performances as actual sold prophy paste formulations available on the market.

Example 2

Purpose

The purpose of this study was to determine the relative abrasion level of prophy pastes.

Procedure

Eight (8) bovine dentin specimens were selected, irradiated and mounted in the usual manner. Treatments were performed following a preconditioning prophy of 30 seconds with flour of pumice using a motor driven prophy cup on the apparatus. Densco® Snap-on prophy cups were used for all reference treatments. The treatments consisted of a 15-second prophy with the appropriate prophy paste. The control treatment was conducted with a (3:2) flour of pumice paste slurry. The platform speed rotated the dentin specimen at 20 rpm and the cup speed was adjusted to 1800 rpm. The load (tension) on the specimens was 250 g. The following test design was used.

A specimen was placed in the recessed holder of the prophylaxis apparatus. The prophy cup was then positioned and the reference abrasive slurry (approximately 0.5 g) placed in the prophylactic cup. The cup was placed on the surface of the specimen and the controlled prophylaxis mechanically administered. Following the prophy, the specimen, the treatment slurry and the prophy cup were carefully transferred to a 10 ounce plastic bottle containing 25 ml deionized water. This procedure was repeated for the remaining 7 radioactive specimens (one bottle per specimen). The lids of the bottles were secured and the contents shaken manually for about 30 seconds. One ml samples were removed and added to 5 ml of scintillation cocktail. The samples were then mixed well and immediately put on the scintillation counter for radiation detection. The specimens and bottles were then rinsed and the prophy procedure repeated using the next treatment regimen.

Calculations

The reference regimen (flour of pumice) was assigned an abrasion value of 1000. The abrasion value of each test regimen sample was calculated using the following formula:

$$\frac{NetExperimentalCPM/g}{MeanControlSandwichNetCPM/g} \times 1000 = RelativeDentinAbrasion$$

Statistical Analysis

Statistical analysis was performed using a one-way analysis of variance model using Sigma Stat Software (3.0). Since significant differences were indicated, the individual means were analyzed by the Student-Newman-Keuls test. Again, Sample S4 represents the inventive paste.

TABLE 3

| Test System | Relative Dentin Abrasion |
| --- | --- |
| Sample S1 | 430.78 ± 33.48* |
| Sample S2 | 333.52 ± 22.71** |
| Sample S3 | 260.18 ± 20.29** |
| Sample S4 | 256.97 ± 19.27** |
| Sample S5 | 251.72 ± 12.53** |

*Mean ± SEM (N = 8)
**Values do not differ significantly (p > 0.05)

TABLE 4

| Specimen Number | Sample S1 | Sample S2 | Sample S3 | Sample S4 | Sample S5 |
|---|---|---|---|---|---|
| 1 | 482.07 | 385.03 | 213.93 | 261.04 | 211.77 |
| 2 | 276.10 | 351.98 | 254.78 | 189.20 | 280.11 |
| 3 | 415.09 | 416.25 | 348.27 | 285.21 | 234.19 |
| 4 | 359.28 | 254.85 | 325.60 | 218.78 | 241.92 |
| 5 | 405.27 | 405.41 | 172.56 | 285.47 | 293.58 |
| 6 | 577.64 | 303.79 | 244.12 | 350.36 | 223.74 |
| 7 | 521.30 | 280.88 | 239.71 | 192.61 | 303.87 |
| 8 | 409.51 | 269.98 | 282.50 | 273.10 | 224.54 |
| MEAN | 430.78 | 333.52 | 260.18 | 256.97 | 251.72 |
| STD. DEV. | 94.70 | 64.24 | 57.40 | 54.51 | 35.45 |
| STD. ERR. | 33.48 | 22.71 | 20.29 | 19.27 | 12.53 |

REA Test on Prophy Pastes

TABLE 5

| Test System | Relative Enamel Abrasion |
|---|---|
| Sample S5 | 9.22 ± 0.73*, ** |
| Sample S2 | 7.73 ± 1.06** |
| Sample S4 | 7.69 ± 0.45** |
| Sample S1 | 7.37 ± 0.68** |
| Sample S3 | 7.12 ± 1.19** |

*Mean ± SEM (N = 8)
*No significant difference between groups (p > 0.05)

TABLE 6

| Specimen Number | Sample S3 | Sample S4 | Sample S5 |
|---|---|---|---|
| 1 | 12.32 | 8.63 | 12.06 |
| 2 | 4.61 | 5.34 | 7.13 |
| 3 | 6.14 | 8.25 | 7.64 |
| 4 | 3.59 | 6.35 | 10.69 |
| 5 | 4.96 | 7.72 | 6.15 |
| 6 | 12.01 | 8.29 | 10.97 |
| 7 | 7.95 | 9.30 | 9.39 |
| 8 | 5.35 | 7.68 | 9.75 |
| MEAN | 7.12 | 7.69 | 9.22 |
| STD. DEV. | 3.36 | 1.28 | 2.07 |
| STD. ERR. | 1.19 | 0.45 | 0.73 |

The results of Example 2 show that the sample S4 shows similar or even lower abrasion values on dentine and enamel as actual sold prophy paste formulations available on the market.

The invention is further set forth in the claims listed below. This invention may take on various modifications and alterations without departing from the scope thereof. In describing embodiments of the invention, specific terminology is used for the sake of clarity. The invention, however, is not intended to be limited to the specific terms so selected, and it is to be understood that each term so selected includes all technical equivalents that operate similarly.

What is claimed is:

1. A prophylactic cleaning product comprising:
   a squeezable tube having a dispense opening therein and a prophylactic paste for cleaning and polishing contained within the squeezable tube, wherein the paste comprises:
   as a sole abrasive and polishing body, expanded perlite in the range of about 40 percent by weight to about 55 percent by weight, wherein the expanded perlite comprises perlite powder with a mean grain size in the range of about 20 to about 70 μm and floaters, and the expanded perlite has a Darcy value in the range of about 0.1 to about 3; about 5 percent by weight or less of a surfactant; and greater than 10 percent by weight water, wherein a compressive force in the range of about 10 N to about 20 N applied to the squeezable tube is effective to dispense the prophylactic paste through the dispense opening.

2. The prophylactic cleaning product of claim 1 wherein the mean grain size of the perlite powder is in the range of about 30 μm to about 60 μm.

3. The prophylactic cleaning product of claim 1 wherein the floaters have a diameter in the range of about 50 μm to about 2000 μm.

4. The prophylactic cleaning product of claim 1 wherein the floaters comprise less than 5 percent by weight of the expanded perlite.

5. The prophylactic cleaning product of claim 1 wherein the surfactant is in the range of about 1 percent by weight to about 5 percent by weight of the paste.

6. The prophylactic cleaning product of claim 5 wherein the surfactant is PEG 40 castor oil.

7. The prophylactic cleaning product of claim 1 wherein the water is in the range of greater than 10 percent by weight to about 35 percent by weight of the paste.

8. The prophylactic cleaning product of claim 1 further comprising a humectant in the range of about 26.5 percent by weight to about 36.5 percent by weight.

9. The prophylactic cleaning product of claim 8 wherein the humectant is glycerin.

10. The prophylactic cleaning product of claim 1 wherein the pellicle cleaning ratio is greater than 85.

11. The prophylactic cleaning product of claim 1 wherein the relative dentin abrasion is less than 265.

12. The prophylactic cleaning product of claim 1 wherein the relative enamel abrasion is less than 8.

13. The prophylactic cleaning product of claim 1 wherein the paste comprises:
   about 40-55 percent by weight expanded perlite wherein the expanded perlite has a Darcy value in the range of about 0.1 to less than 2;
   about 26.5-36.5 percent by weight humectant;
   about 11-25 percent by weight water;
   about 1-5 percent by weight surfactant;
   up to about 3 percent by weight coloring agent;
   up to about 2 percent by weight preservative agent;
   up to about 2 percent by weight alcohol;
   up to about 3 percent by weight flavoring agent;
   up to about 1.5 percent by weight viscosity increasing agent; and
   up to about 3 percent by weight sodium fluoride.

14. The prophylactic cleaning product of claim 1 wherein the dispense opening has a diameter in the range of about 0.5 cm to about 2 cm.

15. The prophylactic cleaning product of claim 1 wherein the dispense opening has a diameter in the range of about 0.7 cm to about 1.5 cm.

16. A method of packaging a prophylactic paste composition in a squeezable tube comprising:
   combining paste components to form a prophylactic paste composition, wherein the paste components comprise:
   about 40-55 percent by weight expanded perlite as a sole abrasive and polishing body wherein the expanded perlite has a Darcy value of less than 2;
   about 26.5-36.5 percent by weight humectant;
   about 11-25 percent by weight water;
   about 1-5 percent by weight surfactant;
   up to about 3 percent by weight coloring agent;
   up to about 2 percent by weight preservative agent;

up to about 2 percent by weight alcohol;

up to about 3 percent by weight flavoring agent;

up to about 1.5 percent by weight viscosity increasing agent;

and up to about 3 percent by weight sodium fluoride, mixing the prophylactic paste composition to achieve a desired viscosity, and filling the squeezable tube through a fill opening with the prophylactic paste composition having the desired viscosity and then sealing the fill opening, wherein the desired viscosity is effective to allow the prophylactic paste composition to be dispensed from a dispense opening opposite the fill opening by applying about 10 N to about 20 N compressive force to the squeezable tube.

17. The method of claim 16 wherein the dispense opening has a diameter in the range of about 0.5 cm to about 2 cm.

18. The method of claim 16 wherein the dispense opening has a diameter in the range of about 0.7 cm to about 1.5 cm.

\* \* \* \* \*